United States Patent [19]

Bell

[11] 4,420,326
[45] Dec. 13, 1983

[54] SYNERGISTIC HERBICIDAL COMPOSITION

[75] Inventor: Allyn R. Bell, Cheshire, Conn.

[73] Assignee: Uniroyal, Inc., New York, N.Y.

[21] Appl. No.: 145,960

[22] Filed: May 2, 1980

Related U.S. Application Data

[63] Continuation-in-part of Ser. No. 972,584, Dec. 22, 1978, abandoned.

[51] Int. Cl.³ .................... A01N 43/64; A01N 43/40
[52] U.S. Cl. ........................................... 71/93; 71/94
[58] Field of Search ................................. 71/93, 94

[56] References Cited

U.S. PATENT DOCUMENTS

| | | | |
|---|---|---|---|
| 3,960,542 | 6/1976 | Plant et al. | 71/94 |
| 3,961,936 | 6/1976 | Westphal et al. | 71/93 |
| 4,032,324 | 6/1977 | Faust et al. | 71/93 |
| 4,095,972 | 6/1978 | Schmidt et al. | 71/93 |
| 4,123,253 | 10/1978 | Hack et al. | 71/93 |

FOREIGN PATENT DOCUMENTS

50-40745  4/1975  Japan ................................. 71/93

OTHER PUBLICATIONS

Eastman et al., "Differences in the Control, etc." (1977), Proc South. Weed Sci. Soc. 30, pp. 39–45.

*Primary Examiner*—Glennon H. Hollrah
*Attorney, Agent, or Firm*—Marvin Bressler

[57] ABSTRACT

A herbicidal composition comprising (I) 2-[1-(2,5-dimethylphenyl)ethyl sulfonyl]pyridine N-oxide and (II) 4-amino-6-tertiary butyl-3-(methylthio)1,2,4-triazin-5(4H)one, useful for control of grasses and broadleaf weeds.

10 Claims, No Drawings

SYNERGISTIC HERBICIDAL COMPOSITION

RELATED APPLICATION

This application is a continuation-in-part of copending U.S. application, Ser. No. 972,584 filed Dec. 22, 1978 now abandoned.

BACKGROUND OF THE INVENTION

Certain sulfinyl and sulfonyl pyridine N-oxides are taught as being effective herbicides. See, for example, U.S. Pat. Nos. 3,960,542, 4,019,893 and 4,050,921 incorporated herein by reference. Similarly, certain triazinones in particular, 4-amino-6-tertiary butyl-3-(methylthio)-1,2,4-triazine-5(4H) one are useful as herbicides. See, for example, U.S. Pat. No. 3,905,801 incorporated herein by reference.

The triazinone is particularly effective in control of weeds in soybeans and potatoes. However, this herbicide does not control grass as well and is also relatively ineffective against broadleaf plants such as jimsonweed and morningglory.

SUMMARY OF INVENTION

It has surprisingly been found that 2-[1-(2,5,dimethylphenyl)ethylsulfonyl]pyridine N-oxide when used in combination with 4-amino-6-tertiary butyl-3-(methylthio)-1,2,4-triazin-5(4H) one is effective against certain grasses and broadleaf weeds notwithstanding the fact that when used independently neither compound shows this activity.

DETAILED DESCRIPTION

This invention relates to a herbicidal composition comprising 2-[1-(2,5,dimethylphenyl)ethylsulfonyl]-pyridine N-oxide, (hereinafter identified as Compound I), 4-amino-6-tertiary butyl-3-(methylthio)-1,2,4-triazin-5(4H) one, (hereinafter identified as Compound II), and an inert diluent.

The use and preparation of Compound I is taught in U.S. Pat. No. 3,960,542 incorporated herein by reference.

The preparation and use of Compound II is taught in U.S. Pat. No. 3,905,801 incorporated herein by reference. As used in the synergistic combination of this invention, the ratio of Compound I to Compound II is from 0.5/1 to 4/1, preferably from 1/1 to 4/1.

Although the invention is described in terms of the activity of the pyridine N-oxide/triazinone (i.e. Compound I/Compound II) controlling jimsonweed and morningglory, the combination exhibits particularly broad and selective herbicidal activity in dicotyledonous crop cultures such as soybeans or potatoes.

Illustrative examples of the weeds which may be controlled include monocots such as fox tail species (Setaria), panicum species (Panicum), crabgrass species (Digitaria), barnyard grass (*Echinochlca crus-galli* L. Beauv.), goosegrass (*Eleusine indica* L. Gaertn), red rice (*Oryza sativa* L.), johnsongrass (*Sorghum halepense* L. Pers.), wild oats (*Avena fatua* L.) and dicots such as pigweed species (Amaranthus), morningglory species (Ipomea), jimsonweed (*Datura stramonium* L.), common lambs quarters (*Chenopodium album* L.), prickly sida (*Sida spinosa* L.), coffeeweed (*Daubentonia texana* Pierce), sickle pod (*Cassia obtusifolia* L.), velvetleaf (*Abutilon theophrasti* Medic), mustard species (Brassica), Pennsylvania smartweed (*Polygonum pensylvanicum* L.) and common ragweed (*Ambrosia artemisiifolia* L.).

The method of using the herbicidal combinations of this invention follows conventional practice and the chemicals are suitably applied as formulations in accordance with conventional agricultural practice. Thus, the composition may be impregnated on finely divided or granular inorganic or organic carriers such as attapulgite clay, sand, silicas including hydrated types, vermiculite, corn cobs, activated carbon or other granular carriers known to the art. The impregnated granules may then be spread on the soil or foliage.

Similarly, the compositions may be formulated as a wettable powder by grinding it into a fine powder and mixing it with inactive powdered carriers (as described above) to which a surface active dispersing agent has been added. Typical powdered solid carriers are the various mineral silicates, e.g. mica, talc, pyrophyllite and clays. The wettable powder may then be dispersed in water and sprayed on the soil surface or weeds. Similarly, an emulsifiable concentrate may be prepared by dissolving the chemical in a solvent such as benzene, toluene or other aliphatic or aromatic hydrocarbon to which a surface active dispersing agent has been added. The emulsifiable concentrate may then be dispersed in water and applied by spraying. Suitable surface active agents are well known to those skilled in the art and reference may be had to McCutcheon's Detergents and Emulsifiers, 1970, Allured Publishing Corp., Ridgewood, N.J.; or Hoffman et al U.S. Pat. Nos. 2,614,916, Cols. 2 to 4 and 2,547,724, Cols. 3 and 4, for example of appropriate surface active agents. The concentration of active chemical in the formulation may vary from 1 to 95 percent; preferably from 40–80 percent by weight. The concentration of active chemical in aqueous dispersions applied to the soil or foliage is almost invariable from 0.002–75 percent by weight. For use as a preemergence herbicide, the composition is applied to soil which contains weed and crop seed (either to the surface of the soil or incorporated into the upper one to three inches (25–75 mm) of soil). The composition may be employed individually or as a mixture of two or more known herbicidal chemicals.

The most suitable rate of application in any given case will depend on such factors as the particular response desired, soil type, soil pH, soil organic matter content, wind velocity, the quantity and intensity of rainfall before and after treatment, the air and soil temperature, light intensity and light duration per day, etc.

Usually $\frac{1}{4}$ lb./acre is used, although as much as 25 pounds per acre may be used. Methods of adjusting application rate to conditions are within the knowledge of those skilled in the art.

For the purpose of readily converting lb./acre into kg./ha. values the following chart may be a guide.

| Lb./Acre | Equals | Kg./ha. |
|---|---|---|
| 1 | | 1.12 |
| $\frac{1}{2}$ | | 0.56 |
| $\frac{1}{4}$ | | 0.28 |
| $\frac{1}{8}$ | | 0.14 |
| 1/16 | | 0.07 |

EXAMPLE I

Preparation Of Wettable Powder Compositions

The formulations below teach the preparation of various wettable powders according to this invention; concentration of active compound of 50 percent by weight in each instance.

| Ingredients | Parts by Weight |
|---|---|
| Formulation I | |
| Compound I | 50 |
| Surfactant (1) | 1 |
| Wetting Agent (2) | 1 |
| Wetting Agent (3) | 2 |
| Solid Carrier (4) | 14 |
| Solid Carrier (5) | 32 |
| | 100 |
| Formulation II | |
| Compound II | 50 |
| Surfactant (6) | 1 |
| Solid carrier (7) | 10 |
| Solid carrier (4) | 35 |
| Wetting Agent (8) | 4 |
| | 100 |
| Formulation III | |
| Compound I | 25 |
| Compound II | 25 |
| Surfactant (9) | 1 |
| Wetting Agent (3) | 3 |
| Solid carrier (4) | 14 |
| Solid carrier (10) | 32 |
| | 100 |

REMARKS:
(1) Alkylaryl polyether alcohol (octylphenoxy polyethoxy ethanol)
(2) Sodium N—methyl-N—palmitoyl taurate
(3) Polymerized sodium salts of alkyl naphthalene sulfonic acid
(4) Kaolinite clay
(5) Hydrated amorphous silica
(6) Dodecylphenol adduct with polyethylene oxide
(7) Diatomaceous silica
(8) Calcium lignin sulfonate
(9) Nonylphenol adduct with polyethylene oxide
(10) Calcium silicate For the above formulations the following general procedure of preparation may essentially be used: the active ingredient(s) plus surfactant is charged to a blender containing solid carrier(s) and wetting agent. Blending is continued to uniformity.

EXAMPLE II

Effectiveness of the Herbicidal Composition for Control of Jimsonweed

As is shown in the following examples, the result obtained with the combination of this invention is indeed a synergistic one.

Formula I and II are further diluted and combined to form aqueous dispersion of various concentrations as follows:

0.01 grams of Formulation I or II are dispersed in 200 ml. of water to yield concentrations of 25 ppm active ingredient. (A concentracion of 25 ppm active ingredient is the equivalent of 1 lb. active/acre when applied to a 6 inch diameter pot as an 80 ml drench.) The dilute aqueous dispersions are identified as Formula IA and IIA respectively.

Further dilutions of Formula IA and IIA will be necessary to obtain the desired active rate for application in the following test:

For example 10 ml of Dispersion IA were combined with 10 ml of Dispersion IIA and then diluted to 80 ml for a final concentration of 3.125 ppm (I)+3.125 ppm (II) or a ratio of 1/8 lb/A (I) to 1/8 lb/A(II). For 1/8 lb/A (I) to 1/4 lb/A (II), 10 ml (IA) were added to 20 ml (IIA) and then diluted to 80 ml.

Preemergence greenhouse soil contained in 6 inch diameter pots was sown with seeds of jimsonweed and was drenched with 80 ml of the desired dispersion. The percent control of weeds compared to untreated checks was determined four weeks after treatment. Table I shows the synergistic effect of the composition prepared in accordance with the above example.

TABLE I

| JIMSONWEED | | |
|---|---|---|
| Rate (Lbs./Acre) | | Actual |
| I | II | I |
| 1/8 | — | 0 |
| 1/4 | — | 0 |
| 1/2 | — | 0 |
| — | 1/8 | 0 |
| — | 1/4 | 30 |

| Mixtures | Actual | Anticipated | Improvement, % |
|---|---|---|---|
| 1/8 + 1/8 | 70 | 0 | ∞ |
| 1/8 + 1/4 | 70 | 30 | 133 |
| 1/4 + 1/8 | 70 | 0 | ∞ |
| 1/4 + 1/4 | 60 | 30 | 100 |

EXAMPLE III

Effectiveness of the Herbicidal Composition for the Control of Morningglory

The composition of this invention was treated for effectiveness on tall morningglory (*Ipomea purpurea* L. Roth) in the manner of Example I. The results are shown in Table II.

TABLE II

| MORNINGGLORY | | |
|---|---|---|
| Rate (Lbs./Acre) | | Actual |
| I | II | I |
| 1/4 | — | 0 |
| 1/2 | — | 0 |
| — | 1/16 | 20 |
| — | 1/8 | 20 |

| Mixture | Actual | Anticipated | Improvement, % |
|---|---|---|---|
| 1/4 + 1/16 | 100 | 20 | 400 |
| 1/4 + 1/8 | 70 | 20 | 250 |
| 1/4 + 1/4 | 95 | 75 | 27 |

As is readily apparent from the above examples, the combinations of this invention show synergistic activity with respect to jimsonweed and morningglory. Similar tests on redroot pigweed, wild oats, green fox tail and barnyard grass showed that the combination was also effective in controlling these weeds.

What is claimed is:

1. A herbicidal composition consisting essentially of a herbicidally effective amount of
   (a) 2-(1-(2,5-dimethylphenyl)ethylsulfonyl)pyridine N-oxide,
   (b) 4-amino-6-tert.-butyl-3-(methylthio)-1,2,4-triazin-5 4(H)one, and
   (c) an intert diluent selected from liquid carriers, solid carriers and mixtures thereof;
   wherein the ratio of (a)/(b) is 0.5/1 to 4/1 by weight.
2. The composition of claim 1 wherein the ratio of (a)/(b) is 1/1 to 2/1.

3. The composition of claim 1 wherein the concentration of (a)+(b) in the inert diluent is from 40-80 percent by weight based on the overall composition.

4. The composition of claim 1 dispersed in water.

5. The composition of claim 4 wherein the concentration of (a) plus (b) is from 0.002-75 percent by weight based on the overall composition.

6. A method for controlling morningglory and jimsonweed which comprises treating soil with a herbicidally effective amount of a composition comprising:
(a) 2-(1-2(2,5-dimethylphenyl)ethyl)sulfonyl)pyridine N-oxide
(b) 4-amino-6-tertiary butyl-3-(methylthio)1,2,4-triazin-5 (4H)one, and
(c) an inert diluent selected from liquid carrier, solid carriers, and mixtures thereof;
wherein the ratio of (a)/(b) is 0.5/1 to 4/1.

7. The method of claim 6 wherein the ratio of (a)/(b) is 1/1 to 2/1.

8. The method of claim 6 wherein the concentration of (a)+(b) in the inert diluent is from 40-80 percent by weight based on the overall composition.

9. The method of claim 6 wherein the composition is dispersed in water.

10. The method of claim 9 wherein the concentration of (a) plus (b) is from 0.002-75 percent by weight based on the overall composition.

* * * * *

UNITED STATES PATENT AND TRADEMARK OFFICE
CERTIFICATE OF CORRECTION

PATENT NO. : 4,420,326
DATED : December 13, 1983
INVENTOR(S) : Allyn R. Bell

It is certified that error appears in the above-identified patent and that said Letters Patent are hereby corrected as shown below:

Column 1, line 26 reading "2-[1-(2,5,dimethyl-" should read --2[1-(2,5-dimethyl- --.

Column 1, line 36 reading "2-[1-(2,5,dimethylphenyl)ethylsulfonyl]-" should read -- 2-[1-(2,5-dimethylphenyl)ethylsulfonyl]- --.

Column 4, line 63 reading "5 4(H)one, and" should read --5(4H)one and--.

Column 5, line 11 reading "(a) 2-(1-2(2,5-dimethylphenyl)ethyl)sulfonyl)pyridine" should read --(a) 2-[1-(2,5-dimethylphenyl)ethylsulfonyl]pyridine--.

Signed and Sealed this

Seventeenth Day of April 1984

[SEAL]

Attest:

GERALD J. MOSSINGHOFF

*Attesting Officer*     *Commissioner of Patents and Trademarks*